(12) United States Patent
Donà

(10) Patent No.: US 12,372,804 B2
(45) Date of Patent: Jul. 29, 2025

(54) SINGLE-LENS GLASSES WITH INTERCHANGEABLE LENSES

(71) Applicant: SAFILO—SOCIETÀ AZIONARIA FABBRICA ITALIANA LAVORAZIONE OCCHIALI S.P.A., Padua (IT)

(72) Inventor: Cristian Donà, Padua (IT)

(73) Assignee: SAFILO—SOCIETÀ AZIONARIA FABBRICA ITALIANA LAVORAZIONE OCCHIALI S.P.A., Padua (IT)

( * ) Notice: Subject to any disclaimer, the term of this patent is extended or adjusted under 35 U.S.C. 154(b) by 570 days.

(21) Appl. No.: 17/711,358

(22) Filed: Apr. 1, 2022

(65) Prior Publication Data

US 2022/0317473 A1 Oct. 6, 2022

(30) Foreign Application Priority Data

Apr. 2, 2021 (IT) .......................... 202021000001715

(51) Int. Cl.
*G02C 1/04* (2006.01)
*G02C 7/10* (2006.01)

(52) U.S. Cl.
CPC .................. *G02C 1/04* (2013.01); *G02C 7/10* (2013.01); *G02C 2200/02* (2013.01); *G02C 2200/08* (2013.01)

(58) Field of Classification Search
CPC .. A61F 9/026; A61F 9/025; A61F 9/02; A61F 2210/009; A61F 2200/02; A61F 2200/08; A61F 2200/04; G02C 7/088; G02C 9/00; G02C 7/10; G02C 11/02; G02C 5/045; G02C 7/00

USPC .................. 351/44, 41, 47, 52, 69, 159.01, 351/159.73–159.76, 178, 57, 86, 90, 96
See application file for complete search history.

(56) References Cited

U.S. PATENT DOCUMENTS

| | | | | |
|---|---|---|---|---|
| 3,896,496 | A * | 7/1975 | Leblanc | A61F 9/025 2/443 |
| 2012/0324638 | A1* | 12/2012 | Tobia | A61F 9/026 351/83 |

(Continued)

OTHER PUBLICATIONS

Translation of DE 2020016106100 (Year: 2020).*

*Primary Examiner* — Dawayne Pinkney
(74) *Attorney, Agent, or Firm* — Carmel Patent Agency; Robert Ballarini (57) ABSTRACT

Interchangeable single-lens glasses include a mount with a front lens-holding frame having a bar extended at supraciliary arches between opposed lateral ends of the frame, and means for removable retention on the bar a single-lens structure extending frontally between the ends. The means for retaining the lens structure on the bar include, at each of the lateral ends, at least a respective first magnet or ferromagnetic material element provided on the frame and a second magnet or ferromagnetic material element provided on the lens in a corresponding position, to cooperate in reciprocal magnetic attraction with the corresponding first element, and, at a central portion of the bar, proximate to a nasal rest area of the mount, a relief protruding frontally from the bar and an opening passing through the lens in a corresponding position, the relief being configured to engage the opening with relative reciprocal locking.

8 Claims, 6 Drawing Sheets

(56) References Cited

U.S. PATENT DOCUMENTS

| | | | |
|---|---|---|---|
| 2013/0185849 A1* | 7/2013 | Laughlin | A61F 9/025 |
| | | | 2/431 |
| 2017/0128267 A1* | 5/2017 | Rees | A61F 9/02 |
| 2019/0113773 A1* | 4/2019 | Langenwalter | G02C 3/003 |
| 2021/0196522 A1* | 7/2021 | Sison | A61F 9/025 |

* cited by examiner

SINGLE-LENS GLASSES WITH INTERCHANGEABLE LENSES

CROSS-REFERENCE TO RELATED APPLICATIONS

This application claims priority to Italian Utility Model Application No. 202021000001715, filed Apr. 2, 2021, the entire contents of which are incorporated by reference herein as if fully set forth.

FIELD OF THE INVENTION

The present invention concerns single-lens glasses with interchangeable lenses.

The invention finds particular application in the specific field of single-lens glasses, i.e. having a single-lens structure, which extends frontally between the opposed lateral ends of the mount, affecting the entire visual field.

The invention is also directed to glasses mainly designed for protective purposes, for example to protect from sunlight, which are fitted with a mount bearing interchangeable type lenses.

BACKGROUND

Single-lens glasses of the type indicated are nowadays widely used, especially for use during sporting activities, where the wrap-around single-lens structure guarantees a wide visual field without obstacles and with any brightness condition.

In the field of single-lens glasses, also known in the jargon of the technical sector of reference as "wrap-around glasses", the need to provide interchangeable type lenses on the same mount is well known, and above all such that they can be easily replaced by the end user.

The advantage of this is in fact that the lenses in the same mount of glasses can be interchanged, if provided for protection from sunlight, with lenses of different coloring for a better adaptation to different light conditions or to guarantee optimal visibility conditions in the most different activities or while practicing different sports disciplines.

Glasses of this type advantageously allow the replacement of the lens both for the correction of any optical parameter, not necessarily linked to visual defects, and for reasons more strictly related to aesthetic appreciation, so as to adapt the same pair of glasses to the different needs of the user.

SUMMARY

The primary aim of the present invention is to propose the structural and functional improvement of the single-lens glasses, in particular in relation to the known systems designed to interchangeably connect the lens to the mount.

In particular, one aim is to provide glasses with a system of coupling the lens to the frame which, although removable in nature, is stable, to adequately constrain the lens to the mount.

Another aim is to make glasses with a constructively simple lens coupling system, which also allows for quick and easy lens fitting and removal as well as being comfortable for the same user, so as to facilitate the interchangeability of the lens while ensuring adequate retention of the lens on the mount.

Another aim is to make single-lens glasses in which the system of coupling the lens to the frame does not alter, or at least affects the aesthetic profile of the glasses as little as possible.

These purposes and still others highlighted below are achieved by the invention by means of glasses made in accordance with the enclosed claims.

In accordance with a first aspect of the invention, the glasses with interchangeable lens comprise a mount having a front lens-holding frame bearing a bar extended at the supraciliary arches between opposed lateral ends of the frame, and means for the removable retention on the bar of a single-lens structure extending frontally between said ends, and wherein the means for retaining the lens structure on the bar comprise, at each of the lateral ends, at least a respective first magnet or ferromagnetic material element provided on the frame and a second magnet or ferromagnetic material element provided on the lens in a corresponding position, to cooperate in reciprocal magnetic attraction with the corresponding first element, and comprise at a central portion of the bar, close to a nasal rest area of the mount, a relief protruding frontally from the bar and an opening passing through the lens in a corresponding position, the relief being susceptible to engage the opening with relative reciprocal locking.

In accordance with another aspect of the invention, the relief is susceptible to engage the opening with substantial shape coupling and at least slight interference.

In accordance with another aspect of the invention, the opening has a closed-contour slotted perimeter profile conformation.

In accordance with another aspect of the invention, the front frame comprises, at each lateral end, a respective wall extending outwardly from the mount in a relation distanced from the bar, the wall bearing an inner surface face facing the bar, on said face there being formed a blind cavity delimiting a seat for housing the corresponding first magnet or ferromagnetic material element.

In accordance with another aspect of the invention, each first magnet or ferromagnetic material element is received in the corresponding seat with surface flush with the inner face of the wall.

In accordance with another aspect of the invention, each second magnet or ferromagnetic material element is housed, with relative locking, in a respective opening passing through the lens thickness.

In accordance with another aspect of the invention, each second magnet or ferromagnetic material element is housed in the respective through opening of the lens with surface flush with the lens surface.

In accordance with another aspect of the invention, each second magnet or ferromagnetic material element is housed in the respective through opening protruding with a portion thereof beyond the surface of the lens.

In accordance with another aspect of the invention, each first magnet or ferromagnetic material element is housed in the corresponding seat remaining in a lowered position with respect to the surface profile of the inner face of the wall, so that the portion of the corresponding second magnet or ferromagnetic material element protruding from the lens surface is accommodated in the seat, following the reciprocal magnetic attraction between the first and second magnet or ferromagnetic material element.

In accordance with another aspect of the invention, the first and second element are configured as magnets and are mounted respectively on the frame and on the lens having opposite polarities to ensure their relative locking by magnetic attraction.

BRIEF DESCRIPTION OF THE DRAWINGS

The characteristics and further advantages of the invention will become clearer from the following detailed description of a preferred but not exclusive embodiment thereof illustrated, by way of non-limiting example, with reference to the accompanying drawings. It is understood, however, that the invention is not limited to the precise arrangements and instrumentalities shown. In the drawings.

DETAILED DESCRIPTION OF THE PREFERRED EMBODIMENTS

With reference to the aforementioned figures, 1 denotes altogether glasses with interchangeable lens, made in accordance with the invention, comprising a mount with a front lens-holding frame 2 bearing a bar 3 which extends substantially at the supraciliary arches, when the glasses are worn, between opposed lateral ends 3a, 3b of the frame.

At the ends 3a, 3b the bar is hingedly articulated with respective lateral temples 4a, 4b (for resting the glasses on the head).

The glasses also comprise means, collectively referred to as 5, for the removable retention of a single-lens structure 6, which extends frontally between the laterally opposed ends 3a, 3b of the frame.

The single-lens structure 6, also known in the eyewear industry as "wrap-around lens", extends to cover both areas of the visual field associated with the eyes, which are connected with a central lens area extended at the nasal rest system. At said central nasal rest area, the bar 3 is interconnected with a support element 7, shaped like an inverted "Y", configured to support a pair of nose pads 8a, 8b.

The lens 6 has an inverted "V"-shaped gap in the central area, the profile of which follows the conformation of the support element 7, in a suitable way such as to prevent the lens in the nasal rest of the mount from interfering with the surface of the nose.

The means for retaining 5 the lens on the frame are provided to removably constrain the lens structure 6 to the frame itself, so as to allow the interchangeability of the lens with other lenses, for example of different coloring and/or having different optical parameters, in order to meet the different needs of the user.

The retaining means 5 comprise, at each of the lateral ends 3a, 3b, a respective first magnet or ferromagnetic material element 9a,9b provided on the frame 2 and a respective second magnet or ferromagnetic material element 10a, 10b provided on the lens 6 in a corresponding position, to cooperate, in reciprocal magnetic attraction with the corresponding first element 9a,9b.

The retaining means 5 further comprise, at a central portion 3c of the bar 3, close to the nasal rest area of the mount, a relief 11 protruding frontally from the bar 3 and an opening 12 passing through the lens in a corresponding position, the relief 11 being susceptible to engage the opening 12 with relative reciprocal locking.

More specifically, the relief 11 protrudes from the bar towards the outside of the mount (opposed to the inner part of the mount which is facing the user's head with the glasses on).

Figure 1:
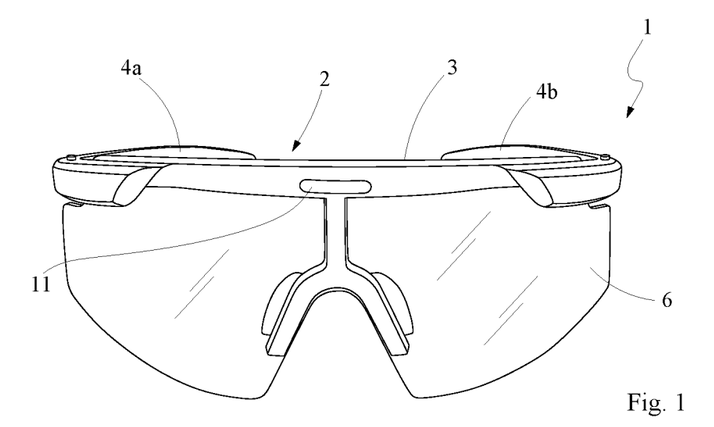
FIG. 1 is a perspective view of an example of glasses made in accordance with the present invention.
Figure 2:
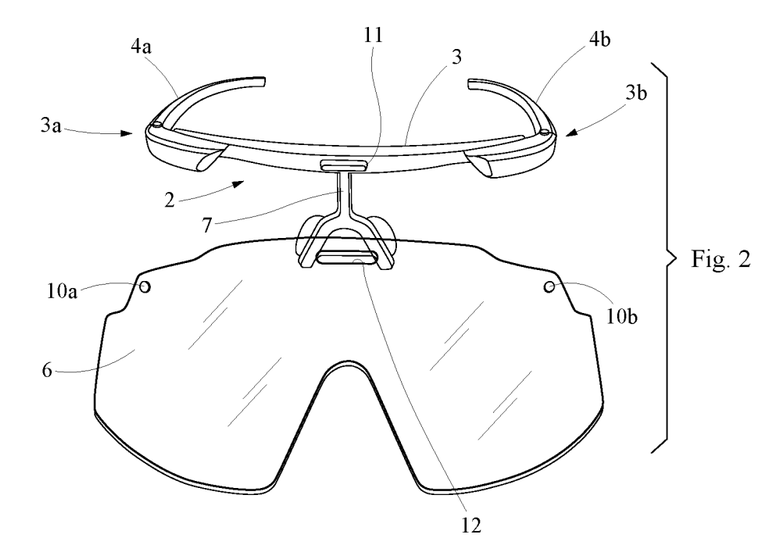
FIG. 2 is a perspective view with detached parts of the glasses of FIG. 1, FIGS. 3 and 4 are perspective views of the lens and mount of the glasses of FIG. 1, respectively.
Figure 3:
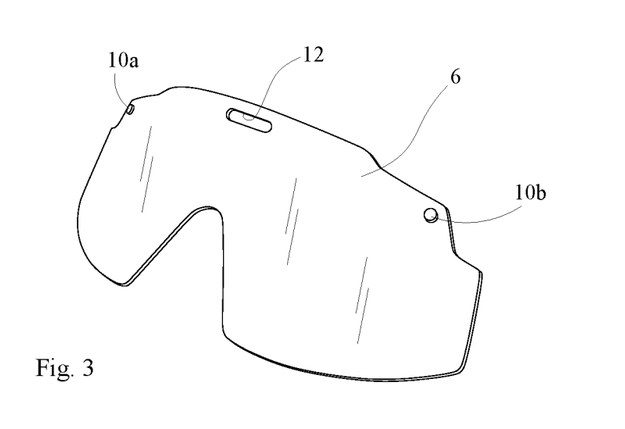
Figure 4:
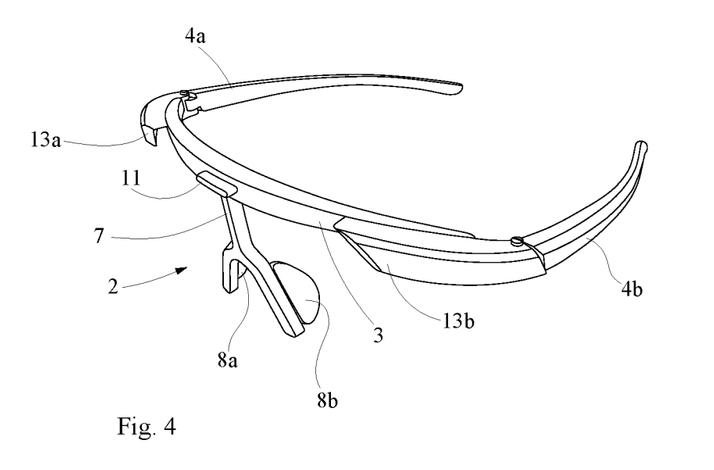
Figure 5:
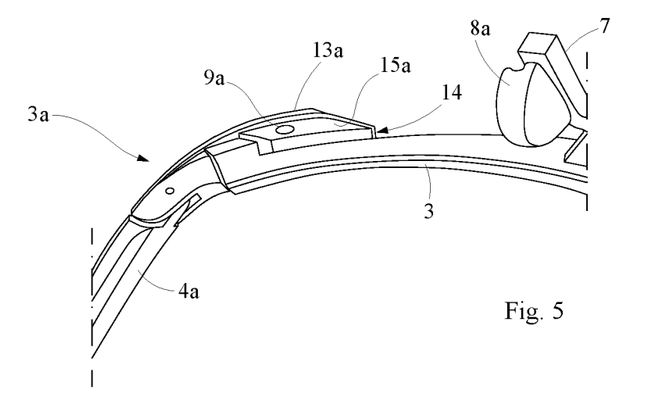
FIG. 5 is a partial sectional perspective view of a detail of the mount of FIG. 4, FIGS. 6 and 7 are partial sectional perspective views of details of the glasses in the preceding figures.
Figure 6:
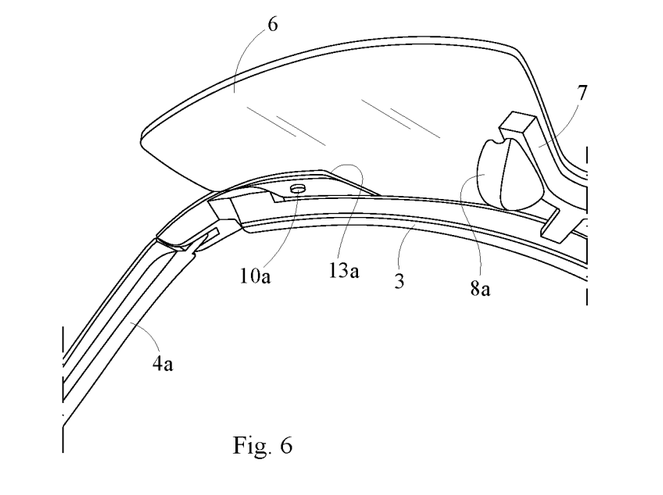
Figure 7:
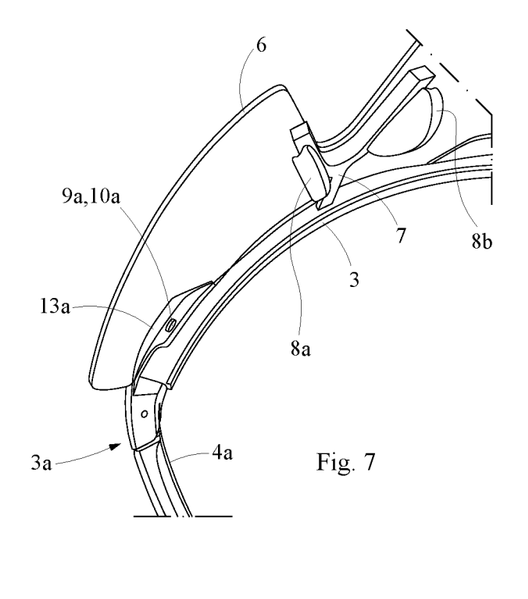
Figure 8:
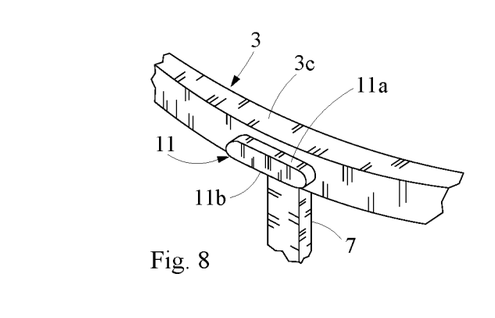
FIG. 8 is a perspective and enlarged scale view of a glasses mount detail of the preceding figures.

The relief 11 is susceptible to engage the opening 12 with a substantial shape coupling. With particular reference to FIG. 8, the relief has an elongated shape delimited by opposed parallel sides 11a, 11b, which are connected, at the opposed axial ends of the relief, with an arcuate surface profile.

The conformation of the opening 12 is correspondingly conceived as an elongated slot, in which the slotted profile has a closed contour.

In a preferred embodiment, it is contemplated that the relief 11 is engaged in the opening 12 in shape coupling with at least slight interference between the surfaces in relative contact, so as to ensure the locking of the coupled parts, while still making the relative disengagement easy if necessary.

The front frame 2 comprises, at each lateral end 3a, 3b of the bar 3, a respective wall 13a,13b extending outwardly from the mount in a relation distanced from the bar 3, so that a channel-shaped space 14 remains delimited between the bar and the wall.

Each wall 13a, 13b is provided with a respective inner surface face 15a, 15b facing the bar 3, on said face there being formed a respective blind cavity 16a, 16b defining a corresponding seat for housing the corresponding first magnet or ferromagnetic material element 9a, 9b.

Each element 9a,9b can be conveniently made cylindrical or discoidal in shape, but other different conformations are possible.

The cavities 16a,16b can conveniently be made as surface recesses formed in the respective walls.

The magnet or ferromagnetic material elements 9a,9b are preferably fixed in the respective housing seats by gluing.

Each magnet or ferromagnetic material element 10a, 10b is housed, with relative locking, in a respective opening or hole 18a, 18b passing through the lens thickness 6.

The magnet or ferromagnetic material elements 10a,10b are preferably fixed in the respective housing openings 18a, 18b by gluing.

Figure 9:
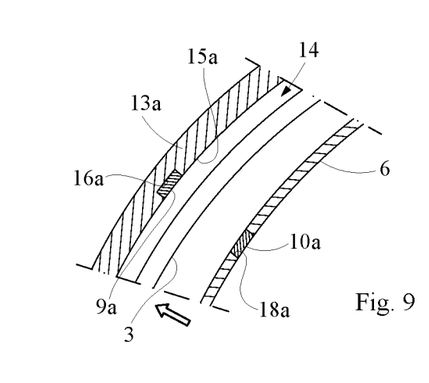
FIG. 9 is a schematic and partial sectional view of details of the mount and of the lens of the glasses of the preceding figures.

In an embodiment (FIG. 9) each first magnet or ferromagnetic material element 9a, 9b is housed in the corresponding seat with surface flush with the inner face 15a, 15b of the wall and each second magnet or ferromagnetic material element 10a, 10b is housed in the respective opening 18a,18b of the lens with surface flush with the lens surface facing the inner face of the wall (with lens mounted on the mount).

Figure 10:
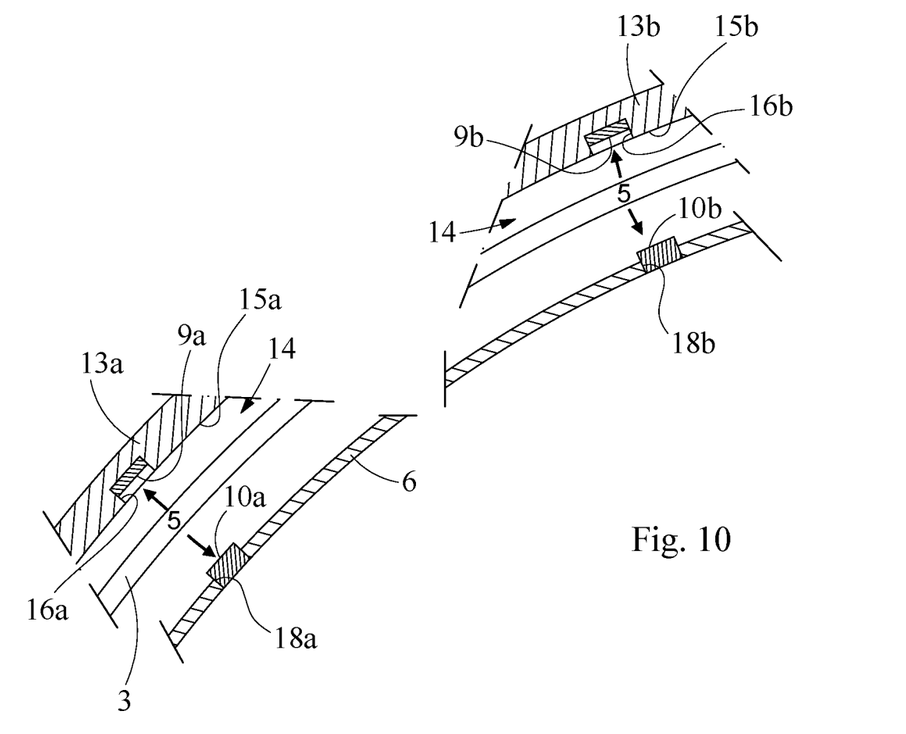
FIG. 10 is a schematic and partial sectional view of the details of FIG. 9 shown in an embodiment variant.

In another embodiment, each first magnet or ferromagnetic material element 9a, 9b is housed in the corresponding seat remaining in a lowered position with respect to the surface profile of the inner face 15a, 15b of the wall, and each second magnet or ferromagnetic material element 10a, 10b is housed in the respective opening 18a, 18b of the lens, with a portion thereof protruding beyond the profile of the lens surface facing the inner face of the wall. With this configuration, schematically illustrated in FIG. 10, by suitably choosing the dimension of the part of element 10a, 10b protruding from the lens and the dimension of the recess of the cavity 16a, 16b not occupied by the element 9a, 9b housed therein, it is possible to obtain that in the relative coupling by magnetic attraction of the elements 9a, 9b with the corresponding elements 10a, 10b, the protruding part of the element 10a, 10b is completely accommodated in the seat housing the corresponding element 9a, 9b, ensuring that the lens surface facing the wall remains close to the inner face of the wall.

In one embodiment, it is envisaged that the first elements 9a, 9b and the second elements 10a,10b are all made as magnets and are accordingly mounted respectively on the frame and on the lens with respective opposite magnetic polarities, in order to ensure their relative locking by magnetic attraction.

Figure 11:
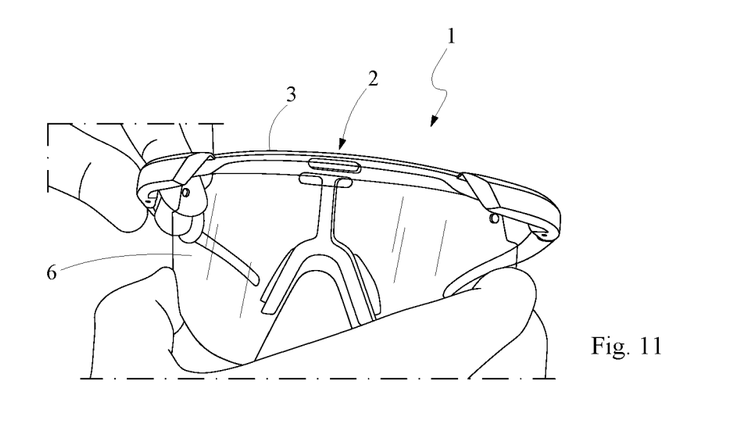
FIGS. 11 to 13 are perspective views of the glasses according to the invention shown in a sequence of respective steps of application of the lens on the mount.
Figure 12:
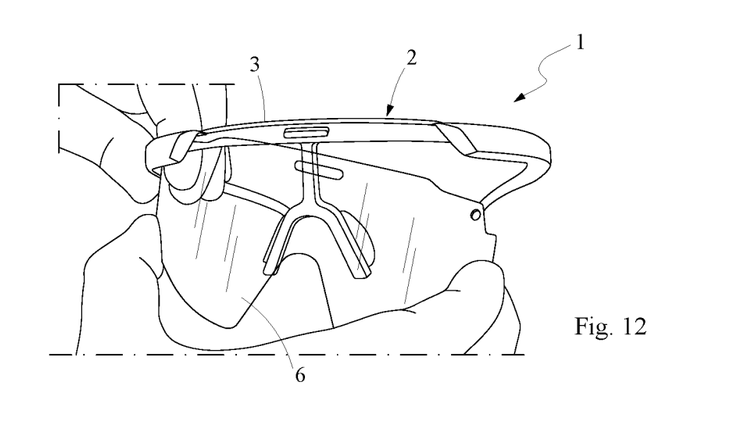
Figure 13:
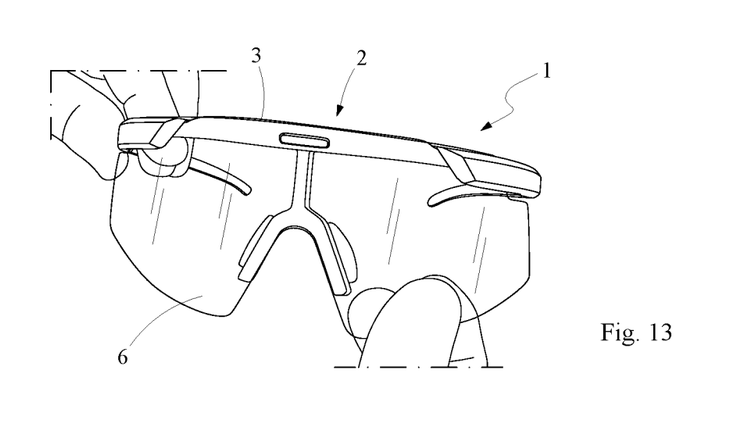

FIGS. 11-13 show in sequence the steps of coupling the lens with the frame of the mount.

In a first step (FIG. 11), the lens 6 is slightly deformed, using its elasticity or flexibility to temporarily accentuate its curvature (for example, by deforming it with one hand while supporting the frame with the other). With this slightly deformed configuration, the lens is brought closer to the frame by bringing the magnet elements 10a,10b towards the respective seats of the corresponding magnet elements 9a, 9b, avoiding in the movement to interfere with the encumbrance of the relief 11. In this way the elements 10a,10b are brought into contact with the corresponding elements 9a, 9b, for the reciprocal magnetic attraction (FIG. 12), and from this position the approach of the slotted opening 12 in the lens to the central relief 11 of the frame begins. The deformation induced on lens 6 is then progressively released, until the lens is brought to rest on the frame, even with the central portion, accomplishing the coupling of the relief with the slot (FIG. 13), and consequently accomplishing the assembly of the lens on the frame.

For the operation of removal of the lens, the steps described are followed in reverse order (FIG. 13 to FIG. 11) until the lens is completely disengaged from the frame.

It should be noted that relief 11 is a major contributor to supporting the weight of the lens, when the latter is coupled with the front frame. In fact, the forces generated by the magnetic couplings alone might not be sufficient in certain embodiments, especially if the magnets themselves are small-sized.

The relief 11 can also be used as a reference to ensure that the lens is centered on the front frame, especially in the initial steps of fitting the lens to the frame.

The relief 11 can also exert a constraining action aimed at preventing any relative movements between the lens and the front frame, in a lateral direction.

In order to best perform its functions, it is convenient that the coupling of the relief with the slotted opening of the lens takes place with a certain degree of interference.

In addition, the relief 11 can also be used as a support for a front decoration or for a logo to be applied to the mount.

At the lateral ends 3a, 3b of the front frame, the respective walls 13a, 13b bearing the seats housing the magnet elements 9a, 9b, advantageously allow to conceal from the front view both the magnetic elements provided on the lens and those provided on the frame, making the design of the glasses more aesthetically pleasant.

The invention thus achieves the proposed objects, achieving numerous advantages with respect to the known solutions.

One advantage is related to the fact that with the glasses according to the invention, a system for coupling the lens to the frame is obtained which, although removable in nature, is stable, suitable for adequately constraining the lens to the mount.

Another advantage is that the system for coupling the lens on the mount is constructively simple, and therefore allows for easy and quick lens fitting and removal operations as well as being comfortable for the user, so as to facilitate the interchangeability of the lens while ensuring adequate retention of the lens on the mount.

Another advantage still lies in the fact that in single-lens glasses in accordance with the invention, the system for coupling the lens to the frontal mount frame does not alter, or at least influences as little as possible, the aesthetic profile of the glasses, mainly due to the fact that no magnet or ferromagnetic material element remain visible when the glasses are worn.

It is understood, therefore, that this invention is not limited to the particular embodiments disclosed, but is intended to cover all modifications which are within the spirit and scope of the invention as defined by the appended claims; the above description; and/or shown in the attached drawings.

The invention claimed is:

1. Single-lens glasses with interchangeable lenses comprising:
    a mount with a front lens-holding frame bearing a bar extended at supraciliary arches between opposed lateral frame ends,
    means for removable retention on said bar of a single-lens structure extending frontally between said ends,
    wherein said means for retaining the lens structure on said bar comprise:
    at each of said lateral ends at least a respective first magnet or ferromagnetic material element provided on the frame and a second magnet or ferromagnetic material element provided on the lens in a corresponding position, to cooperate in reciprocal magnetic attraction with the corresponding first magnet or ferromagnetic material element, the second magnet or ferromagnetic material element being housed, with relative locking, in a respective opening passing through the lens thickness, and
    at a central portion of the bar, proximate to a nasal rest area of the mount, a relief protruding frontally from the bar and an opening passing through the lens in a corresponding position, the relief being configured to engage the opening with relative reciprocal locking, and
    wherein the front frame comprises, at each lateral end, a respective wall extending outwardly from the mount in a relation distanced from the bar, so that a channel-shaped space remains delimited between the bar and the wall,
    the wall bearing an inner surface face facing the bar, on said face there being formed a blind cavity delimiting a seat for housing the corresponding first magnet or ferromagnetic material element.

2. The glasses according to claim 1, wherein said relief is configured to engage said opening with substantial shape coupling and at least slight interference.

3. The glasses according to claim 1, wherein said opening has a closed-contour slotted perimeter profile conformation.

4. The glasses according to claim 1, wherein each first magnet or ferromagnetic material element is received in the corresponding seat with surface flush with the inner face of the wall.

5. The glasses according to claim 1, wherein each second magnet or ferromagnetic material element is housed in the respective through opening of the lens with surface flush with the lens surface.

6. The glasses according to claim 1, wherein each second magnet or ferromagnetic material element is housed in the respective through opening protruding with a portion thereof beyond the surface of the lens.

7. The glasses according to claim 6, wherein each first magnet or ferromagnetic material element is housed in the corresponding seat remaining in a lowered position with respect to the surface profile of the inner face of said wall, so that the portion of the corresponding second magnet or ferromagnetic material element protruding from the lens surface is accommodated in said seat, following the reciprocal magnetic attraction between said first and second magnet or ferromagnetic material element.

8. The glasses according to claim 1, wherein said first and second magnet or ferromagnetic material element are configured as magnets and are mounted respectively on the frame and on the lens having opposite polarities to ensure their relative locking by magnetic attraction.

* * * * *